United States Patent [19]
Ohriner

[11] Patent Number: 6,132,677
[45] Date of Patent: Oct. 17, 2000

[54] METHOD FOR MAKING RADIOACTIVE METAL ARTICLES HAVING SMALL DIMENSIONS

[75] Inventor: Evan K. Ohriner, Knoxville, Tenn.

[73] Assignee: Lockheed Martin Energy Research Corporation, Oak Ridge, Tenn.

[21] Appl. No.: 09/299,245

[22] Filed: Apr. 26, 1999

[51] Int. Cl.[7] .................................................. B21C 23/00
[52] U.S. Cl. ........................... 419/67; 29/17.2; 72/253.1; 72/255
[58] Field of Search ........................ 419/5, 67; 29/17.2; 72/253.1, 255; 252/625

[56] References Cited

U.S. PATENT DOCUMENTS

| | | | |
|---|---|---|---|
| 5,624,372 | 4/1997 | Liprie | 600/3 |
| 5,807,231 | 9/1998 | Liprie | 600/3 |
| 5,833,593 | 11/1998 | Liprie | 600/3 |
| 5,840,008 | 11/1998 | Klein et al. | 600/3 |
| 5,857,956 | 1/1999 | Liprie | 600/7 |
| 5,858,452 | 1/1999 | Leader et al. | 427/97 |
| 5,871,436 | 2/1999 | Eury | 600/3 |
| 5,871,530 | 2/1999 | Williams et al. | 607/122 |
| 5,873,811 | 2/1999 | Wang et al. | 600/5 |

*Primary Examiner*—Ngoclan Mai
*Attorney, Agent, or Firm*—Williams, Morgan & Amerson, P.C.

[57] ABSTRACT

A method for making a radioactive article such as wire, includes the steps of providing a metal article having a first shape, such a cylinder, that is either radioactive itself or can be converted to a second, radioactive isotope by irradiation; melting the metal article one or more times; optionally adding an alloying metal to the molten metal in order to enhance ductility or other properties; placing the metal article having the first shape (e.g., cylindrical) into a cavity in the interior of an extrusion body (e.g., a cylinder having a cylindrical cavity therein); extruding the extrusion body and the article having the first shape located in the cavity therein, resulting in an elongated extrusion body and an article having a second shape; removing the elongated extrusion body, for example by chemical means, leaving the elongated inner article substantially intact; optionally repeating the extrusion procedure one or more times; and then drawing the elongated article to still further elongate it, into wire, foil, or another desired shape. If the starting metal is enriched in a radioactive isotope or a precursor thereof, the end product can provide a more intense radiation source than conventionally manufactured radioactive wire, foil, or the like.

30 Claims, No Drawings

METHOD FOR MAKING RADIOACTIVE METAL ARTICLES HAVING SMALL DIMENSIONS

This invention was made with Government support under contract DE-AC05-96OR22464 awarded by the U.S. Department of Energy to Lockheed Martin Energy Research Corporation. The Government has certain rights in this invention.

BACKGROUND OF THE INVENTION

The present invention relates to a method of making radioactive metal articles having small dimensions, such as wire, foil, and rods. In particular, the present invention concerns a method in which the concentration of radioactive species in the wire or other article is not limited by the concentrations of such species or their precursors naturally occurring in the metal from which the wire is made.

Certain medical treatments make use of radioactive materials in the form of wire or filaments. For example, radiation therapy for cancer patients sometimes makes use of radioactive wires that can be implanted or inserted in the patient's body to provide a therapeutic dose of radiation to an area of the body, i.e., to destroy tumor cells. For example, the radioactive wire can be implanted into a solid tumor in the patient's body, or inserted into a blood vessel, where it can be left for a time sufficient to provide the desired dose of radiation to the intended site in the patient's body.

Another medical procedure that could make use of radioactive wire is the prevention of restenosis (gradual reclosure) in coronary arteries after angioplasty. It is believed that application of radiation to a region of a coronary artery that has been dilatated by angioplasty can inhibit restenosis, by inhibiting cell growth in that region.

The Ir-192 isotope, with a half-life of 79 days, is one material that is currently used in the medical treatment of certain cancers. In one method now in use, short lengths of natural iridium wire are irradiated to produce Ir-192, by neutron capture of Ir-191. The iridium wire segments are sealed within a cavity at the end of a larger diameter wire of another material, typically a nickel-titanium alloy. The larger diameter wire can then be implanted or inserted into the target area of the patient's body.

However, the abundance of Ir-191 in natural iridium is only 37%. This limits the concentration of Ir-192 that can be generated by irradiation of standard iridium wire. There is a need for more intense radiation sources for therapy, in order to provide higher doses of radiation to a site in a patient's body, or to provide a given dosage of radiation in a shorter time. In some cases there is a need for smaller diameter radiation sources of the same intensity, in order to further localize the region of tissue affected during a radiation treatment.

One possibility for producing iridium wire comprising a higher concentration of Ir-192 is to form the wire in the first instance from iridium that has already been enriched in Ir-191 compared to natural iridium, followed by irradiation of the wire to convert the Ir-191 to Ir-192. However, this has not been practical in the past because of the high cost of the enriched iridium (presently about $10,000/g) and the limited quantities available (typically less than 100 g). Although there are a limited number of commercial producers of natural iridium wire, there is no previously existing practical method of fabricating wire starting with such limited quantities of material.

A need exists for improved methods of making radioactive wire that can produce a wire having an enhanced concentration of radioactive species from very small amounts of starting materials.

SUMMARY OF THE INVENTION

The present invention concerns a method for making radioactive articles, and is especially well-suited for making such articles that have at least one small dimension, such as wire, foil, and small-diameter rods. In this method, a metal article having a first shape is provided. The first shape can be, for example, a cylinder if the desired end product is wire or a rod. Alternatively, the first shape can be a bar having a rectangular cross-section if the desired end product is foil or a thin rectangular bar.

A preferred method of making the initial metal article is to first provide a mass of molten metal that comprises a first isotope that is radioactive or that can be converted to a second, radioactive isotope by irradiation, and then to mold the molten metal into a cylinder or other desired shape. The metal preferably is melted more than one time prior to being molded into a cylinder or other desired shape. It is especially preferred to produce the mass of molten metal by forming a compact of powdered metal that comprises the first isotope, and then melting the compact. In certain specific embodiments of the method, the compact of powdered metal is sintered at a temperature of at least about 1000° C. before being melted. It is also preferred to add a second metal to the molten metal, to form an alloy that has better ductility than the metal in the molten compact will have if cooled by itself.

The metal article comprises a first isotope that is either radioactive itself or can be converted to a second, radioactive isotope by irradiation. For example, if the metal article is made of iridium and comprises some Ir-191, that isotope can be converted to Ir-192 after the article is in its final, desired configuration.

The metal article having the first shape (e.g., cylindrical) is placed into a cavity in the interior of an extrusion body. In a preferred embodiment of the method, the extrusion body is a metal cylinder having a cylindrical cavity therein. Molybdenum is an especially preferred metal to use for the extrusion body.

The method next involves extruding the extrusion body and the article having the first shape located in the cavity therein. This results in an elongated extrusion body and an article having a second shape. If the first shape is cylindrical, the second shape will usually also be cylindrical (although this will depend on the die through which the extrusion occurs), but the article having the second shape will be longer and have a smaller diameter than the article having the first shape. Alternatively, if the article having the first shape was a bar having a rectangular cross-section, then the article having the second shape can also be a bar with a rectangular cross section, but it will be longer than the article having the first shape, and will have a smaller cross-sectional area.

The extrusion procedure optionally can be repeated one or more times, so that the article having the second shape is extruded to form an article having a third shape, which optionally can be further extruded to form an article having a fourth shape, and so on. Each extrusion will progressively reduce the thickness of the article, making it closer to its desired final configuration. These additional extrusions can be done with the elongated extrusion body still in place around the article having the second shape. The elongated extrusion body can serve as the extrusion body for the second extrusion. Alternatively, a second, new extrusion body can be used. In that embodiment, the article having the second shape can remain in place in the interior of the elongated extrusion body, and the elongated extrusion body can be placed in a cavity in the interior of the new, second extrusion body. As yet another alternative, the elongated extrusion body from the first extrusion can be removed, and the article having the second shape placed in a cavity in the interior of the second extrusion body, and then the second extrusion can be performed. Similar alternatives can be used for third, fourth, and subsequent extrusions if needed.

After extrusion is completed, the elongated extrusion body (or bodies) is then removed, leaving behind the article having the second shape (or third shape, etc.) substantially intact. This removal can be done by chemically dissolving or etching away the material of the extrusion body, for example by contacting it with an acid that will dissolve or etch molybdenum but will not do so to any substantial extent to iridium.

The article having the second shape (or third shape, etc.) can then be drawn to further elongate it, into wire, foil, or another desired shape. If the article having a first shape is a first cylinder, the article having a second shape is usually a second cylinder that has a smaller diameter and a greater length than the first cylinder, and the drawing step can convert the second cylinder into wire. Alternatively, if the article having a first shape is a first bar having a rectangular cross-section, the article having a second shape is a second bar having a smaller rectangular cross-section, and the second bar can be drawn into foil or an even thinner bar.

Thus, one embodiment of the method can further comprise the steps of placing the article having the second shape into a cavity in the interior of a second extrusion body; followed by extruding the second extrusion body and the article having the second shape located in the cavity therein, thereby producing an elongated second extrusion body and an article having a third shape. The elongated second extrusion body can be removed, prior to the drawing of the article having the third shape.

One specific embodiment of the present invention is a method for making an iridium wire that comprises Ir-192. This method comprises the steps of:

(a) forming a compact of powdered iridium that comprises Ir-191;

(b) sintering the compact;

(c) melting the compact, thereby providing a mass of molten iridium;

(d) molding the molten iridium into a cylinder;

(e) placing the iridium cylinder into a cavity in the interior of a first extrusion body;

(f) extruding the first extrusion body and the iridium cylinder located in the cavity therein, thereby producing an elongated first extrusion body and elongated iridium cylinder;

(g) removing the elongated first extrusion body;

(h) placing the elongated iridium cylinder into a cavity in the interior of a second extrusion body;

(i) extruding the second extrusion body and the elongated iridium cylinder located in the cavity therein, thereby producing an elongated second extrusion body and a further elongated iridium cylinder;

(j) removing the elongated second extrusion body;

(k) drawing the further elongated iridium cylinder to further elongate it into wire; and (l) irradiating the wire to convert Ir-191 to Ir-192.

Preferably the first and second extrusion bodies are each molybdenum cylinders having cylindrical cavities therein. The compact of powdered iridium preferably comprises a sufficient concentration of Ir-191 so that the irradiated wire comprises Ir-192 in a concentration sufficient to provide a therapeutic dose of radiation to a human in which the wire is inserted or implanted.

It is also preferred in this embodiment of the invention that a second metal, such as cerium, be added to the molten iridium, thereby forming an alloy having greater ductility than pure iridium. One way of adding the alloying metal is to add to the molten iridium a master alloy that comprises a major amount of iridium and a minor amount of cerium. In this context, "major" means more than 50% by weight, and "minor" means less than 50% by weight.

The compact of powdered iridium can comprise about 10–200 grams, or even less. One of the advantages of the method of the present invention is its ability to work with such small amounts of starting material. This is especially important in view of the very high cost of enriched iridium. It is preferred that the powdered iridium starting material be enriched in Ir-191 (i.e., comprises Ir-191 in a concentration greater than 37% by weight). This allows the end product to have a higher concentration of Ir-192 than can be achieved by irradiation of conventionally made iridium wire. The abundance of Ir-191 in naturally occurring iridium is about 37%, and thus the limit on Ir-192 concentration in such conventional wire is also about 37%.

The wire, foil, and other articles made by the present invention are useful in medical procedures, such as radiation therapy of cancer patients.

DETAILED DESCRIPTION OF SPECIFIC EMBODIMENTS

The method of the present invention can be used to make radioactive articles having at least one small dimension (e.g., thickness or diameter). Examples of such articles are wire, small diameter rods, very thin bars, and foil. The method can suitably begin with a powdered metal, such as powdered iridium. Such powdered metals are commercially available, for example from Oak Ridge National Laboratory (Oak Ridge, Tenn.). A small amount, for example 10–200 g of the powdered metal, can be pressed into a compact, and then preferably is sintered. The sintering can optionally be done in more than one step, such as a pre-sintering step followed by sintering at a higher temperature. Equipment and conditions for forming compacts form powdered metal and sintering such compacts are known to those skilled in the art.

The sintered compact is then melted, and preferably melted several times. One suitable method for melting the compact is arc melting. During one or more of these steps when the metal is in a molten state, one or more alloying metals can be added, in order to produce a metal having enhanced properties, such as improved ductility. Cerium is one such alloying metal that can be added to molten iridium for purposes of the present invention. The amount of cerium added will typically be no greater than about 50 ppm by weight of the metal in the composition.

The metal used in the present invention should be one that can yield a radioactive final product. This can be accomplished by having the starting metal contain radioactive isotopes, preferably isotopes that emit gamma radiation. An alternative that is presently preferred is to instead have the starting metal powder contain an isotope than can be converted, after manufacturing of the wire or other end product, into another isotope that provides the desired radioactivity. One preferred example is the use of iridium that comprises some quantity of the isotope Ir-191, which can be converted to the medically useful isotope Ir-192 by irradiation and neutron capture. Naturally occurring iridium contains about 37% by weight Ir-191. Therefore, in the embodiment of the present invention where the metal is iridium, it is especially preferred that the starting iridium be enriched in Ir-191, to a concentration greater than 37%. Typically the isotope enrichment is performed using calutrons. Use of Ir-191 enriched iridium as a starting material allows the production of wire, foil, and the like that produce more intense emissions per gram of metal, which can be beneficial in medical and other uses.

Optionally one or more additional metals can also be included that are themselves radioactive or that can be converted to a radioactive isotope by irradiation. Thus, it is possible for the final product to contain more than one radioactive species.

After the metal has been melted one or more times, and any desired alloying metal has been added, the molten metal is molded into an article having a first shape. If the desired end product is wire, then the first shape will usually be a cylinder. However, it should be understood that articles having other shapes could be used to produce wire or other end products. For example, instead of a cylinder with a perfectly circular cross-section, an approximately cylindrical bar that has a hexagonal or octagonal cross-section could be used instead. The extrusion steps would tend to make the cross-section more circular, and the end product could still be wire, whether or not its cross-section was perfectly circular. Alternatively, by controlling the extent of the extrusion and drawing, the end product could be a rigid rod instead of a flexible wire. Another alternative is to use as the article having the first shape a bar having a rectangular instead of circular cross-section. Extrusion of such a bar would produce a bar that still has a generally rectangular cross-section, but thinner and longer than the original bar. Drawing of such a thinned bar could produce either a still thinner bar or a sheet of foil. Other configurations are possible as well.

The article having the first shape, which for discussion purposes will be assumed to be an iridium cylinder, is then placed into an extrusion body. The extrusion body is preferably a generally cylindrical molybdenum "can" having a cylindrical cavity in its interior. The iridium cylinder can be inserted into this cavity in the molybdenum can by removing an end cap from the can, inserting the cylinder, and then replacing the end cap. The combined assembly of the extrusion body (molybdenum can) and the iridium cylinder contained therein are then extruded through a die, so that both the extrusion body and the iridium cylinder have their diameter reduced and their length increased.

The elongated extrusion body may then be removed, preferably by chemical means. For example, a concentrated solution of mineral acids can be used to chemically remove the molybdenum extrusion body, while leaving the elongated iridium cylinder largely unaffected. If the diameter of the iridium cylinder has been sufficiently reduced, then the next step in the manufacturing process can be drawing. However, in many situations it will be necessary to have one or more additional extrusion steps prior to drawing. In such cases it is not necessary to remove the extruded first body material, and the entire extruded first body can be placed in a cavity of the second extrusion body. Therefore, the elongated iridium cylinder can be placed into a second molybdenum extrusion body (or "can") having a cylindrical cavity in its interior. The second extrusion body may or may not have a smaller outer diameter than the first extrusion body.

The second extrusion body and the elongated iridium cylinder therein are then extruded through a second die. The second extrusion body (or both the first and second extrusion bodies) can then be removed, for example by the same chemical means described above, and the iridium cylinder, which is now further elongated, can either be extruded again, or can proceed to the drawing step.

Procedures and apparatus for drawing an elongated iridium cylinder into wire are known to those skilled in the art. After the drawing step is complete, the resulting wire can be cut into any desired length. The same is true if the drawn product is foil or a thin rod instead of wire.

Although Ir-192 is an especially preferred radioactive isotope in the wire or other end product of the present method, other radioactive isotopes are suitable as well. Suitable examples include Cs-137, Co-57, Co-60, Sr-89, Sr-90, P-32, Y-90, Au-198, I-125, Pd-103, Se-75, Ru-106, Yb-169, and Am-241.

Various aspects of the present invention can be further understood from the following example. However, the specific details in the example should not be interpreted as limiting the scope of the invention.

EXAMPLE

A 50 g button of natural iridium was prepared from a larger iridium button that had been previously fabricated from natural iridium powder. The 50 g button was remelted by tungsten arc nonconsumable-arc melting in an atmosphere of high-purity argon and alloyed with 20 ppm by weight of natural cerium. The resulting button was remelted and then drop-cast to produce a 8.9-mm-diameter by 25-mm-high cylinder. This cylinder was placed in a cavity within a molybdenum extrusion body and hot-extruded at ratio of 10:1. The molybdenum was chemically dissolved, and the resulting iridium rod was placed inside the cavity of another molybdenum extrusion can and again hot-extruded. After cutting the molybdenum to locate the end of the resulting iridium wire, one end of the extruded bar was heated and swaged to produce a length of wire of about 10 cm with a reduced diameter, to be used as the leader section in the subsequent drawing. The remainder of the molybdenum was chemically dissolved, and the wire was then drawn from about 1.1 mm diameter to produce a single 0.60-mm-diameter by 2.1 -m-long wire. The details of each of the processing steps are described below.

Starting Material

A 50 g button was cut from a 500-g button of pure iridium which had been electron-beam melted eight times at a vacuum pressure of about 0.01 torr. The 500 g button had been made previously from seven powder compacts of pure iridium of about 80 g each, which had been pressed in a steel die at a pressure of 355 MPa. The compacts were presintered in dry hydrogen gas for 1 h at 1000° C., and then sintered in vacuum for 4 h at 1500° C.

A single powder compact of about 50 g could be pressed with the same die and presintered and sintered in the same manner. The main technical issue involves material loss during the electron-beam melting. Typical mass loss during electron-beam melting is 7%, with about one-half of this loss as splatter and the other half as vaporization. This is by far the largest potential loss of iridium in the processing and is discussed in detail below.

Arc Melting

The arc-melting is performed using a nonconsumable, thoriated tungsten electrode in an evacuated chamber which is backfilled with two-third atmospheric pressure of high-purity argon. An addition of 20 ppm by weight of cerium was made using Ir-2% Ce added as a master alloy. Cerium acts to minimize grain growth in iridium and improves ductility. The cerium facilitates subsequent process steps and is at a sufficiently low level to have no adverse effect on other properties of the wire. The button was melted five times in a water-cooled copper hearth for about 1 min each time at 20 VDC and a current of 300 A. The button was then melted in another similar furnace and allowed to drop through an opening in the hearth to fill a copper mold. The casting cavity was 8.9 mm (0.35 in.) diameter and 25.4 mm (1 in.) high with a hot-top section tapered at 11° over 7.9 mm (⁵⁄₁₆ in.) height. The metal loss during melting was 0.2 g of the 50.66 g melted. After cutting the hot-top section, the ingot weighed 34.2 g and showed no shrinkage cavity. The remaining material consisted of a skull of 4.0 g and a hot-top section of 10.2 g. The loss in cutting was 2.0 g.

Extrusion

The extrusion was performed in two steps to reduce the diameter of the material from 8.9 to 1.07 mm (0.35 to 0.042 in.) and to increase the length from 25 to 840 mm (1 to 33 in.). In both steps, the iridium was placed inside a cavity in a heavy wall molybdenum can of 48 mm (1.9 in.) OD, machined from molybdenum bar. The cavity was machined to a diameter about 0.6 mm (0.025 in.) greater than that of the iridium. The nose of the cans were tapered at 45° to a 25-mm-diameter (1-in.-diameter) flat. The cavity was located 19 mm (0.75 in.) behind the tapered section of the can, and the end cap thickness was 25 mm (1 in.). The iridium and the molybdenum can were cleaned with alcohol, and the molybdenum end cap was screwed onto the can. The cans were then coated with a paste mixture of 200 mesh glass powder in a sodium silicate solution, which was thoroughly dried. The extrusion was preheated for 2 h at 1425° C. and extruded through a die opening of 16.3 mm (0.64 in). The die had a 45° semi-entrance angle and was coated with partially stabilized zirconia. The maximum load on the extrusion press was 1.13 MN (127 tons), as compared to a maximum limit of 2.85 MN (320 tons) for this size billet. The extruded bar was immediately reheated to 1300° C. for about 15 min and swaged to straighten the extrusion. The diameter of the rod after swaging was 15.0 mm (0.59 in.). The molybdenum was dissolved in aqueous solution of 45% concentrated nitric acid and 5% concentrated sulfuric acid by volume. The iridium rod recovered from the extrusion had a total length of 20 cm (8 in.). The diameter was nominally 2.8 mm (0.11 in.) although the ends of the rod flared to diameters as large as 5 mm (0.2 in.). The oversize portion extending 38 mm (1.5 in.) from each end was cut off to leave a rod of 127 mm (5 in.) length with a diameter of 2.7 to 2.9 mm (0.105 to 0.115 in.). The rod was electrolytically cleaned in a saturated aqueous solution of KCN for 5 min to remove the reaction product formed between the iridium and the molybdenum can during preheating of the extrusion.

The cleaned rod was placed in a second molybdenum can with a cavity diameter of 3.56 mm (0.140 in.). The extrusion conditions were identical to the first extrusion with the exception that the preheat temperature was reduced to 1350° C. to minimize any reaction between the iridium rod and the molybdenum can during preheating. The extrusion load of 2.46 MN (276 tons) was significantly higher than for the first extrusion as a result of the lower preheat temperature. The molybdenum was cut from the leading end of the extrusion until the location of the starting point of the encased iridium wire was located, about 12 cm (5 in.) from the nose. The leading end of the extruded bar was reheated to 1200° C. and swaged with a series of dies to reduce the diameter of the leading end to 8.9 mm (0.35 in.). The molybdenum was then dissolved as described above. The resulting wire had a total length of 84 cm (33 in.). The leading 10 cm (4 in.) had a diameter of 0.76 mm (0.030 in.) while the remainder of the wire ranged in diameter from 1.07 to 1.12 mm (0.042 to 0.044 in.).

Wire Drawing

The drawing of the wire was performed using steel dies with tungsten-carbide inserts. The die and the wire were both lubricated using a micronized graphite spray and were both heated to 600° C. prior to drawing. The wire passed through a stainless steel muffle which contained flowing argon gas. The drawing die sizes are listed in Table 1. The measured wire diameter produced after drawing through each die is also shown. The wire was drawn at rate of about 7 mm/s (16 in./min). The first two wire draws reduced the section thickness only in limited regions of the wire, due to the nonuniformity in the as-extruded wire. During the drawing through the nominal 0.030 in. die, the total length of the wire of 1.37 m (54 in.) exceeded the working length of the straight draw bench being used. The draw was interrupted and the wire regripped at midlength using the roughened steel plates used normally to grip the wire for drawing. The portion of the wire which was gripped was examined for evidence of scratching. No effect of the regripping could be seen at 30× magnification using a binocular microscope. A similar regripping was used for all subsequent draws. An effort was made to regrip at the same location at the midlength of the wire, even as the length of the wire increased with each draw.

After drawing through the nominal 0.030 in die, the leading end was too large to pass through the remaining dies. It was intended that the swaging of the extrusion with the molybdenum can still intact would produce a leading end of 0.6 mm (0.024 in.) diameter. Since this did not occur, it was necessary to reduce the diameter of the leading end by another means. Without the molybdenum to act as a thermal barrier and a source of thermal mass, hot-swaging was not possible. The only practical method was to chemically remove some of the iridium. This was done by submersing about 12 cm (5 in.) of the leading end of the wire into the KCN solution described above and electrolytically removing the material. This required dissolution for about 3 h at 10 VAC with a current of about 25 A. About 0.6 g of iridium was removed. A small additional removal was performed prior to the final draw to bring the diameter of the leading end to 0.56 mm (0.022 in.). The product of the drawing operations was a single 0.60-mm-diameter by 2.2-mm-length (0.0236-in.-diameter by 88-in.-length) wire.

TABLE 1

Die sizes used and resulting wire diameters during hot-drawing of iridium

| Nominal die size (in.) | Measured wire diameter | |
|---|---|---|
| | (in.) | (mm) |
| 0.044 | Not uniform | Not uniform |
| 0.043 | Not uniform | Not uniform |
| 0.041 | 0.043 | 1.09 |
| 0.040 | 0.041 | 1.04 |
| 0.039 | 0.039 | 0.99 |
| 0.0375 | 0.0377 | 0.96 |
| 0.036 | 0.0357 | 0.91 |
| 0.034 | 0.0345 | 0.88 |
| 0.032 | 0.0320 | 0.81 |
| 0.030 | 0.0305 | 0.77 |

TABLE 1-continued

Die sizes used and resulting wire diameters during hot-drawing of iridium

| Nominal die size (in.) | Measured wire diameter | |
|---|---|---|
| | (in.) | (mm) |
| 0.029 | 0.0290 | 0.74 |
| 0.028 | 0.0283 | 0.72 |
| 0.027 | 0.0274 | 0.70 |
| 0.0265 | 0.0265 | 0.67 |
| 0.025 | 0.0252 | 0.64 |
| 0.024 | 0.0244 | 0.62 |
| 0.023 | 0.0235 | 0.60 |

Cleaning and Sampling

A sample of the wire was cleaned in an acid solution of seven parts concentrated nitric acid, three parts concentrated hydrochloric acid, and one part concentrated hydrofluoric acid, all by volume, at room temperature. The wire remained an unusually dark gray color, which may be due to carbon lubricant remaining on the surface. The samples were placed in an iridium alloy cup and heated in air at 850° C. for 15 min to remove residual carbon lubricant. Following this treatment, the samples appeared black, while the iridium cup appeared only slightly tarnished. The samples were wiped with alcohol to remove some of the surface tarnish. They were again placed in the iridium alloy cup and heated in hydrogen at 850° C. for 1 h to reduce any iridium oxide at the surface to metal. The samples exhibited a light gray metallic luster characteristic of iridium surfaces.

From the initial 50 g melted, the processing produced 13.5 g of wire, 31.4 g of material for remelting, and 5 g of loss from cutting and electrolytic material removal operations. The relatively high cutting losses are the result of using a cutting blade with a width of 1.5 mm (0.060 in.) on a high-speed cut-off saw. The material for remelting consisted of 14.1 g from the melting operation and 17.3 g from the extrusion processes.

This method can modified by use of different can materials, different chemical and cleaning methods, different iridium alloy compositions, and different processing temperatures and conditions. Room temperature drawing of iridium wire is also possible. The method can also be used for make rods and foils from small quantities of iridium powder.

The preceding description of specific embodiments of the present invention is not intended to be a complete list of every possible embodiment of the invention. Persons skilled in this field will recognize that modifications can be made to the specific embodiments described here that would be within the scope of the present invention.

What is claimed is:

1. A method for making a radioactive article, comprising the steps of:
   (a) providing a metal article having a first shape, the metal article comprising a first isotope that is radioactive or that can be converted to a second, radioactive isotope by irradiation;
   (b) placing the metal article having the first shape into a cavity in the interior of an extrusion body;
   (c) extruding the extrusion body and the article having the first shape located in the cavity therein, thereby producing an elongated extrusion body and an article having a second shape;
   (d) removing the elongated extrusion body; and
   (e) drawing the article having the second shape to further elongate it.

2. The method of claim 1, wherein the article having a first shape is a first cylinder, the article having a second shape is a second cylinder that has a smaller diameter and a greater length than the first cylinder, and the second cylinder is drawn into wire in step (e).

3. The method of claim 1, wherein the article having a first shape is a first bar having a rectangular cross-section, the article having a second shape is a second bar having a rectangular cross-section, and the second bar is drawn into foil in step (e).

4. The method of claim 1, wherein the metal comprises iridium, the first isotope is Ir-191, and the radioactive isotope into which the Ir-191 can be converted is Ir-192.

5. The method of claim 1, wherein the metal article having a first shape is provided by:
   providing a mass of molten metal that comprises a first isotope that is radioactive or that can be converted to a second, radioactive isotope by irradiation; and
   molding the molten metal into a cylinder.

6. The method of claim 5, wherein the mass of molten metal is provided by forming a compact of powdered metal that comprises the first isotope, and melting the compact.

7. The method of claim 6, wherein the compact of powdered metal is sintered at a temperature of at least about 1000° C. before being melted.

8. The method of claim 6, wherein the metal is melted more than one time prior to being molded into a cylinder.

9. The method of claim 5, wherein a second metal is added to the molten metal, thereby forming a ductility-enhanced alloy.

10. The method of claim 1, wherein the extrusion body is a metal cylinder having a cylindrical cavity therein.

11. The method of claim 10, wherein the extrusion body is a molybdenum cylinder having a cylindrical cavity therein.

12. The method of claim 1, wherein after step (c), the article having a second shape is extruded at least one additional time in an extrusion body.

13. The method of claim 12, wherein the at least one additional extrusion is done with the elongated extrusion body of step (d) still in place around the article having the second shape.

14. The method of claim 12, wherein the at least one additional extrusion is done with the article having a second shape located in a cavity in the interior of the elongated extrusion body from step (c), and with the elongated extrusion body located in a cavity in the interior of a second extrusion body.

15. The method of claim 1, wherein the elongated extrusion body is removed in step (d) by dissolving it in a substance that will leave the elongated cylinder substantially intact.

16. The method of claim 1, wherein the article having the second shape is placed into a cavity in the interior of a second extrusion body.

17. The method of claim 16, further comprising the step of extruding the second extrusion body and the article having the second shape located in the cavity therein, thereby producing an elongated second extrusion body and an article having a third shape.

18. The method of claim 17, wherein the elongated second extrusion body is removed prior to the drawing of the article having the third shape.

19. The method of claim 1, wherein the metal article having a first shape further comprises a third isotope that is radioactive or that can be converted to a fourth, radioactive isotope by irradiation.

20. The method of claim 1, wherein the method produces an article comprising a radioactive isotope selected from the group consisting of Ir-192, Cs-137, Co-57, Co-60, Sr-89, Sr-90, P-32, Y-90, Au-198, I-125, Pd-103, Se-75, Ru-106, Yb-169, and Am-241.

21. A method for making an iridium wire that comprises Ir-192, comprising the steps of:

(a) forming a compact of iridium that comprises Ir-191;

(b) melting the compact, thereby providing a mass of molten iridium;

(c) molding the molten iridium into a cylinder;

(d) placing the iridium cylinder into a cavity in the interior of an extrusion body;

(e) extruding the extrusion body and the iridium cylinder located in the cavity therein, thereby producing an elongated extrusion body and elongated iridium cylinder;

(f) removing the elongated extrusion body; and (g) irradiating the iridium to convert Ir-191 to Ir-192.

22. The method of claim 21, further comprising the step of drawing the elongated iridium cylinder to further elongate it into wire prior to the irradiation of step (g).

23. A method for making an iridium wire that comprises Ir-192, comprising the steps of:

(a) forming a compact of powdered iridium that comprises Ir-191;

(b) sintering the compact;

(c) melting the compact, thereby providing a mass of molten iridium;

(d) molding the molten iridium into a cylinder;

(e) placing the iridium cylinder into a cavity in the interior of a first extrusion body;

(f) extruding the first extrusion body and the iridium cylinder located in the cavity therein, thereby producing an elongated first extrusion body and elongated iridium cylinder;

(g) removing the elongated first extrusion body;

(h) placing the elongated iridium cylinder into a cavity in the interior of a second extrusion body;

(i) extruding the second extrusion body and the elongated iridium cylinder located in the cavity therein, thereby producing an elongated second extrusion body and a further elongated iridium cylinder;

(j) removing the elongated second extrusion body;

(k) drawing the further elongated iridium cylinder to further elongate it into wire; and (l) irradiating the wire to convert Ir-191 to Ir-192.

24. The method of claim 23, wherein the first and second extrusion bodies are each molybdenum cylinders having cylindrical cavities therein.

25. The method of claim 23, wherein the compact of powdered iridium comprises a sufficient concentration of Ir-191 so that the irradiated wire comprises Ir-192 in a concentration sufficient to provide a therapeutic dose of radiation to a human in which the wire is inserted or implanted.

26. The method of claim 23, wherein a second metal is added to the molten iridium, thereby forming an alloy having greater ductility than pure iridium.

27. The method of claim 26, wherein the second metal is cerium.

28. The method of claim 27, wherein the second metal is added in the form of a master alloy that comprises a major amount of iridium and a minor amount of cerium.

29. The method of claim 23, wherein the compact of powdered iridium comprises no more than about 200 grams.

30. The method of claim 23, wherein the powdered iridium comprises Ir-191 in a concentration greater than 37% by weight.

* * * * *